(12) United States Patent
Guala

(10) Patent No.: US 7,588,563 B2
(45) Date of Patent: *Sep. 15, 2009

(54) MEDICAL CONNECTOR

(75) Inventor: Gianni Guala, Turin (IT)

(73) Assignee: Industrie Borla S.p.A., Moncalieri (Turin) (IT)

( * ) Notice: Subject to any disclaimer, the term of this patent is extended or adjusted under 35 U.S.C. 154(b) by 261 days.

This patent is subject to a terminal disclaimer.

(21) Appl. No.: 11/492,537

(22) Filed: Jul. 24, 2006

(65) Prior Publication Data

US 2007/0088327 A1    Apr. 19, 2007

(30) Foreign Application Priority Data

Jul. 25, 2005   (IT) .......................... TO2005A0516

(51) Int. Cl.
*A61M 25/16* (2006.01)

(52) U.S. Cl. .................. 604/535; 604/533; 604/534; 604/538; 604/539

(58) Field of Classification Search .................. 604/533, 604/534, 535, 537–539, 246–249, 32, 33, 604/256, 905

See application file for complete search history.

(56) References Cited

U.S. PATENT DOCUMENTS 5,645,538 A   7/1997   Richmond
5,702,374 A * 12/1997  Johnson ....................... 604/533
6,508,807 B1 * 1/2003  Peters ......................... 604/533
7,347,458 B2 * 3/2008  Rome et al. .................. 285/384
2001/0042850 A1 11/2001 Cote, Sr.
2002/0082586 A1  6/2002 Finley et al.

FOREIGN PATENT DOCUMENTS

WO    WO 01/07102 A2    2/2001
WO    WO 01/07102 A2 *  2/2001
WO    WO 03/030987 A1   4/2003

OTHER PUBLICATIONS

European Search Report, Application No. EP 06 11 7302, Nov. 15, 2006.

* cited by examiner

*Primary Examiner*—Kevin C Sirmons
*Assistant Examiner*—Laura C Schell
(74) *Attorney, Agent, or Firm*—Heslin Rothenberg Farley & Mesiti P.C.; Victor A. Cardona, Esq.

(57) ABSTRACT

Medical connector comprising a tubular body with an inlet fitting and an outlet fitting of the female luer-lock type connected to the body in a rotary and axially translatable way between a retracted position and an advanced position. One-directional detent assemblies enable rotation of the outlet fitting in one direction in the retracted position and in the opposite direction in the advanced position.

7 Claims, 6 Drawing Sheets

US 7,588,563 B2

MEDICAL CONNECTOR

CROSS REFERENCE TO RELATED APPLICATIONS

This application is a claims priority from Italian Patent Application No. TO2005A000516 filed on Jul. 25, 2005, the entire disclosure of which is incorporated herein by reference.

FIELD OF THE INVENTION

The present invention relates to medical connectors, of the type comprising a tubular body having an inlet fitting and an outlet fitting of the female luer-lock type that can be engaged by screwing with a complementary male luer-lock fitting, for example of a medical line.

STATE OF THE PRIOR ART

Traditionally, in medical connectors of this type, the female luer-lock connector is rigidly joined to the body: the complementary male luer-lock fitting of the medical line can thus be freely screwed and unscrewed with respect to the female luer-lock fitting of the connector. This involves, once the complementary male luer-lock fitting has been screwed in the female luer-lock fitting of the connector, risks of accidental or in any case undesirable unscrewing, which could lead to the detachment of the medical line from the connector with the serious consequences that could derive therefrom in use.

SUMMARY OF THE INVENTION

The purpose of the present invention is to overcome the aforesaid drawback and to provide a medical connector of the type defined above that will be designed to prevent effectively, in use, risks of any accidental detachment of the medical line.

According to the invention, the above purpose is achieved thanks to the fact that the female luer-lock fitting is connected to the body of the connector in a rotary and axially translatable way from a retracted position to an advanced position against the action of elastic thrust means, and to the fact that first and second one-directional detent means are provided, of which the first prevent rotation between said luer-lock fitting and said body in a first direction of rotation corresponding to screwing of said complementary male luer-lock fitting to said female luer-lock fitting when said female luer-lock fitting is set in said retracted position, and the second prevent rotation between said female luer-lock fitting and said body in a second direction of rotation corresponding to unscrewing of said complementary male luer-lock fitting from said female luer-lock fitting when said female luer-lock fitting is set in said advanced position.

Thanks to this arrangement, screwing between the female luer-lock fitting of the connector and the complementary male luer-lock fitting is obtained normally as in the case of traditional medical connectors of the same type, whilst unscrewing thereof can be performed only following upon a translation of the female luer-lock fitting towards the inside of the body, performed positively against the action of the elastic thrust means. In the absence of said positive and voluntary translation, a rotation of unscrewing of the complementary male luer-lock fitting simply causes a corresponding rotation of the female luer-lock fitting with respect to the body of the connector: this advantageously prevents any accidental or undesirable separation between the connector according to the invention and the medical line connected to the complementary male luer-lock fitting.

BRIEF DESCRIPTION OF THE DRAWINGS

The invention will now be described in detail with reference to the annexed plate of drawings, which are provided purely by of way of non-limiting example and in which.

DETAILED DESCRIPTION OF THE INVENTION

Figure 1:
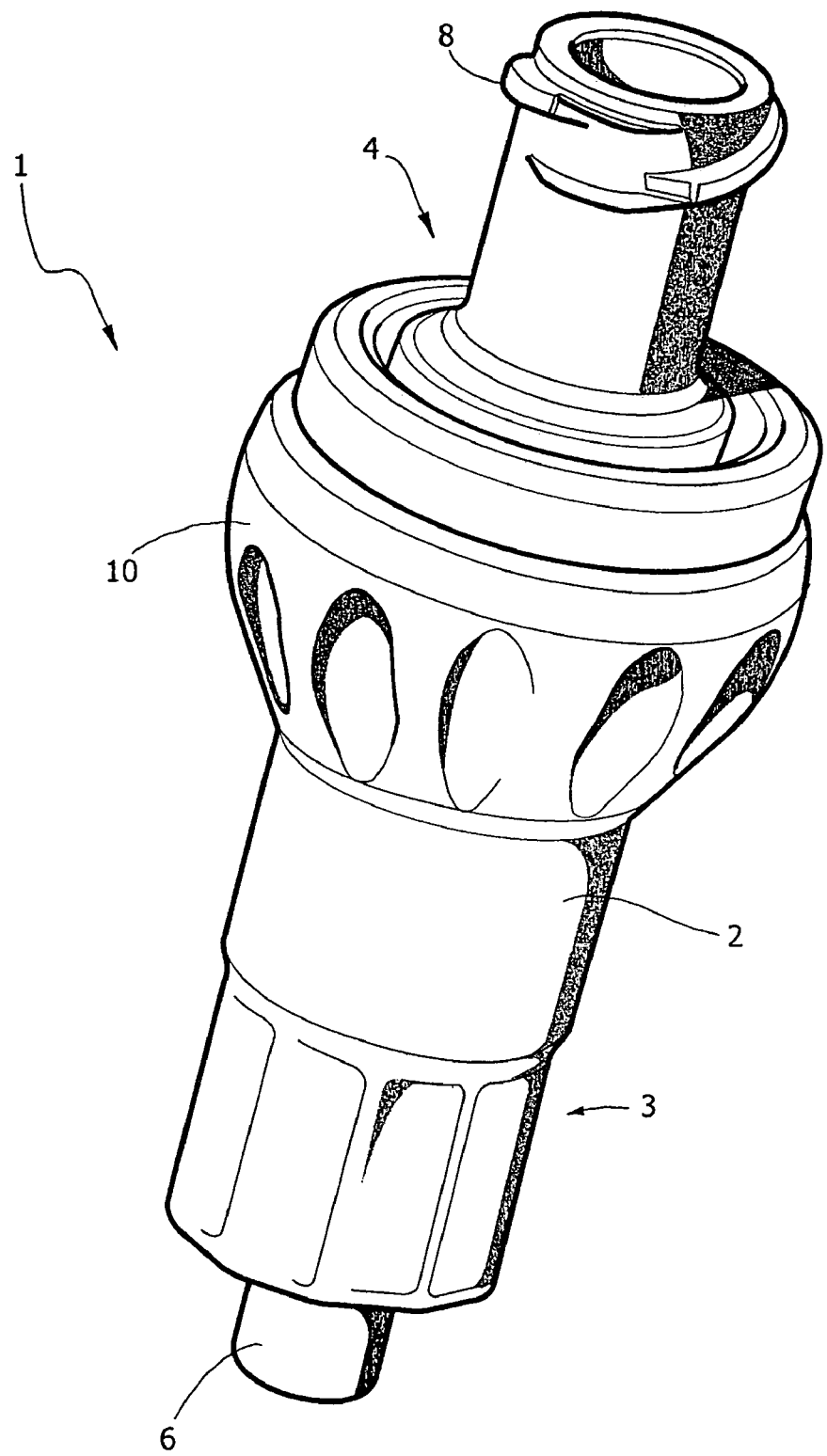
FIG. 1 is a schematic perspective view of a medical connector according to the invention.

With reference to the drawings, number 1 designates as a whole a medical connector according to the invention, basically comprising a tubular body 2 provided, coaxially with respect to its ends, with an inlet fitting 3 and an outlet fitting 4 that is connectable to a pipe of a medical line, for example an infusion line. The above-described components of the medical connector 1 are all made of moulded plastic material.

Figure 2:
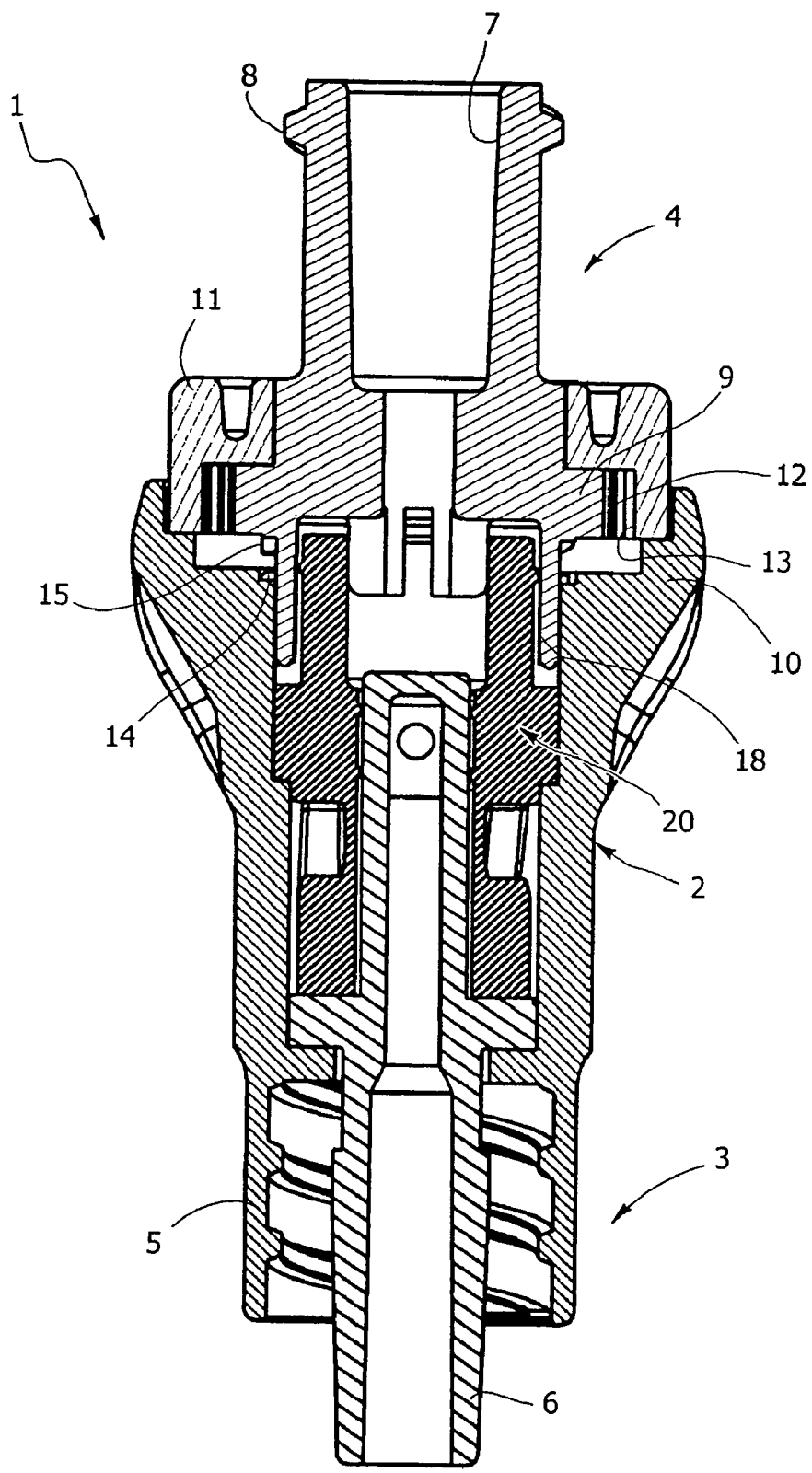
FIG. 2 is an axial cross-sectional view of the connector represented in a first operative position.

With reference now in greater detail to FIG. 2, in the case of the example illustrated the inlet fitting 3 is of the male luer-lock type, with an external hollow part 5, internally threaded and formed integrally with the body 2, and an internal tubular part 6 that can slide axially with respect to the external part 5. It should be noted that the illustrated conformation of the male luer-lock fitting 3 is not significant for the purposes of the present invention, and indeed forms a subject of a parallel Italian patent application filed on the same date in the name of the present applicant. The inlet fitting 3 could consequently present any different conformation, and even consist of a simple tubular element directly connectable to a pipe.

The outlet fitting 4 consists of a fitting of the female luer-lock type, formed in a generally conventional way, with an internal cavity having a conical surface 7 and an external thread 8. It can be connected in use to a male luer-lock fitting of a conventional type, connected to a medical line and having a conformation generally corresponding to that of the inlet fitting 3 (except for the fact that the corresponding external and internal parts are normally formed in a single piece), and is consequently not illustrated herein.

Figure 4:
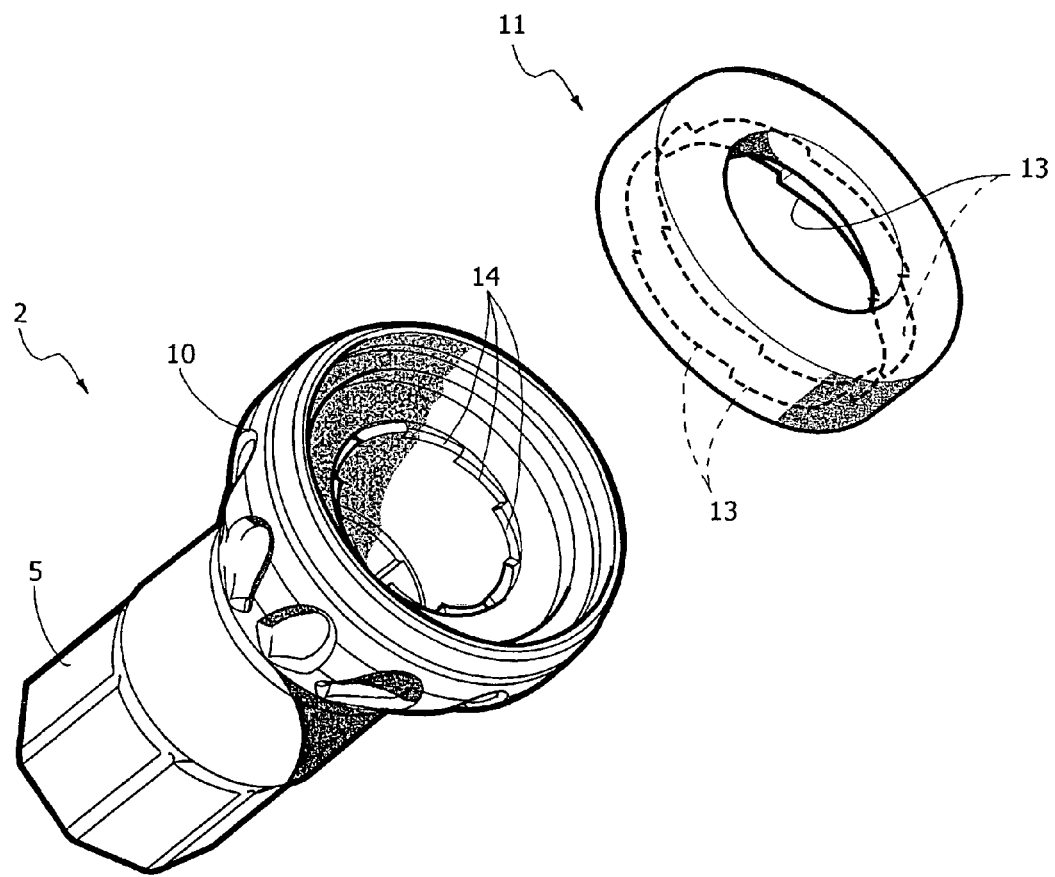
FIG. 4 is an exploded perspective view at a larger scale of the body of the connector.

According to the fundamental characteristic of the invention, the female luer-lock fitting 4 is connected to the body 2 of the connector 1 in a rotary and axially translatable way. For this purpose, it is formed with an intermediate radial annular flange 9 set axially between a widened end part 10 of the body 2 and an annular collar 11 rigidly connected to said widened part 10, for example by means of welding or other systems. The intermediate flange 9 is formed integrally with a ring of pawl-like sprung teeth 12, designed to co-operate, in the way clarified in what follows, with a ring of saw teeth 13 formed integrally within the collar 11, in the way represented in detail in FIG. 4. As will be seen in what follows, the pawls 12 and the teeth 13 define a first one-directional detent assembly, via which the female luer-lock fitting 4 can rotate with respect to the body 2 of the connector 1 only in a first direction of rotation corresponding to screwing on said female luer-lock fitting 4 of the complementary male luer-lock fitting.

Figure 5:
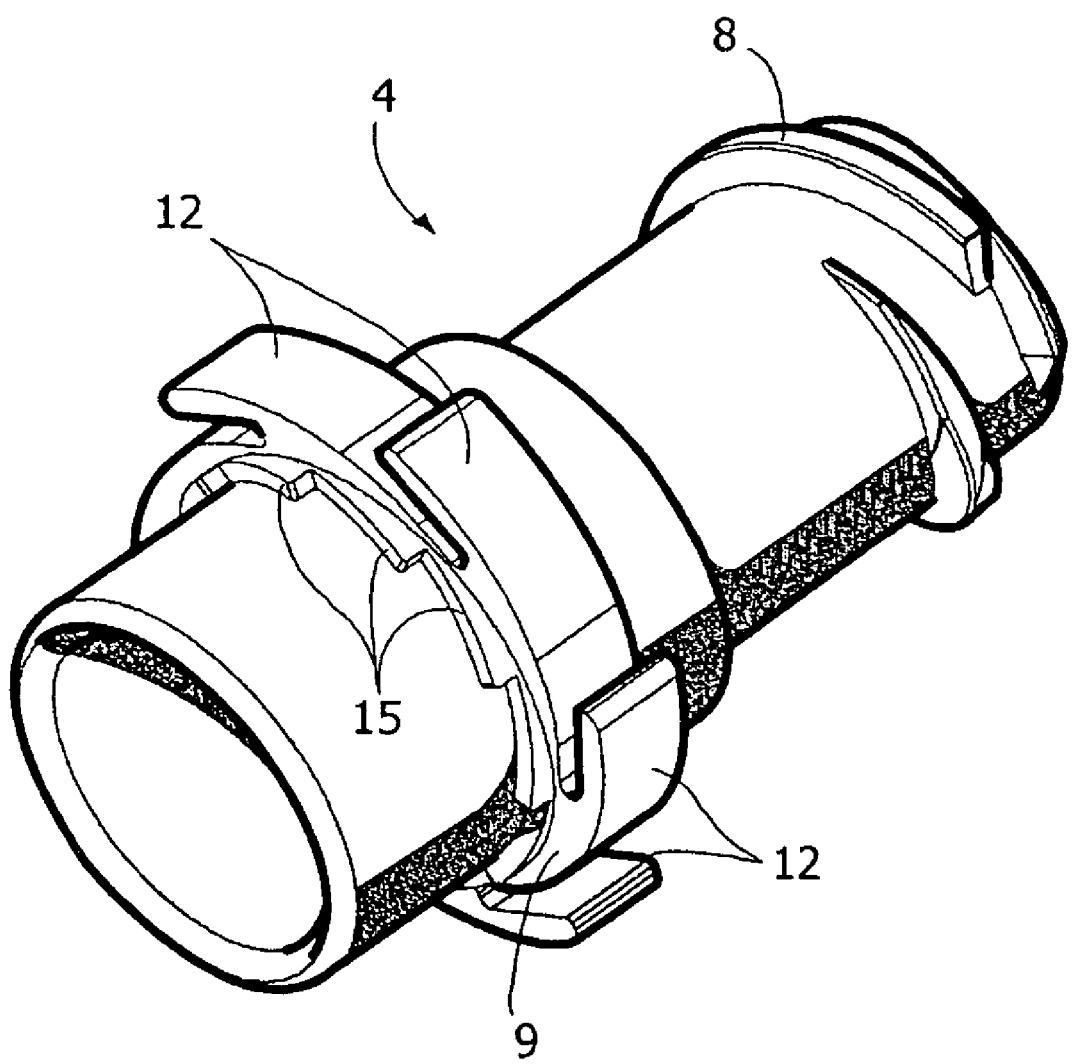
FIG. 5 is a perspective view at a larger scale of the female luer-lock fitting of the connector.

With reference once again to FIG. 4, the widened part 10 of the body 2, which has an ergonomic conformation, with recesses designed to facilitate manual gripping thereof, is in turn formed internally with a ring of detent teeth 14, set opposed and axially staggered with respect to the saw teeth 13 of the collar 11, with which there is designed to co-operate, in the way clarified in what follows, a ring of saw teeth 15, which are also formed integrally with the fitting 4 underneath the sprung pawls 12, in the way clearly visible in FIG. 5. The teeth 14 and 15 define a second one-directional detent assembly designed to enable rotation of the fitting 4 with respect to the body 2 only in a second direction of rotation, opposite to the first, to enable, as will be seen, unscrewing of the complementary male luer-lock fitting screwed on the outlet fitting 4.

The intermediate flange 9 with the sprung pawls 12 and the saw teeth 15 is housed with axial play between the enlarged part 10 of the body 2 and the collar 11. This enables the outlet fitting 4 to translate axially with respect to the body 2 between the retracted position, represented in FIG. 2, and the advanced position, represented in FIG. 3. An elastic element, designated as a whole by 15, constituted conveniently by a sleeve made of elastomeric material inserted within the body 2 between the fittings 3 and 4, tends normally to keep said fitting 4 in the retracted position of FIG. 1. An elastic axial compression of the sleeve 15 enables the outlet fitting 4 to translate from the retracted position of FIG. 2 to the advanced position of FIG. 3.

Figure 6:
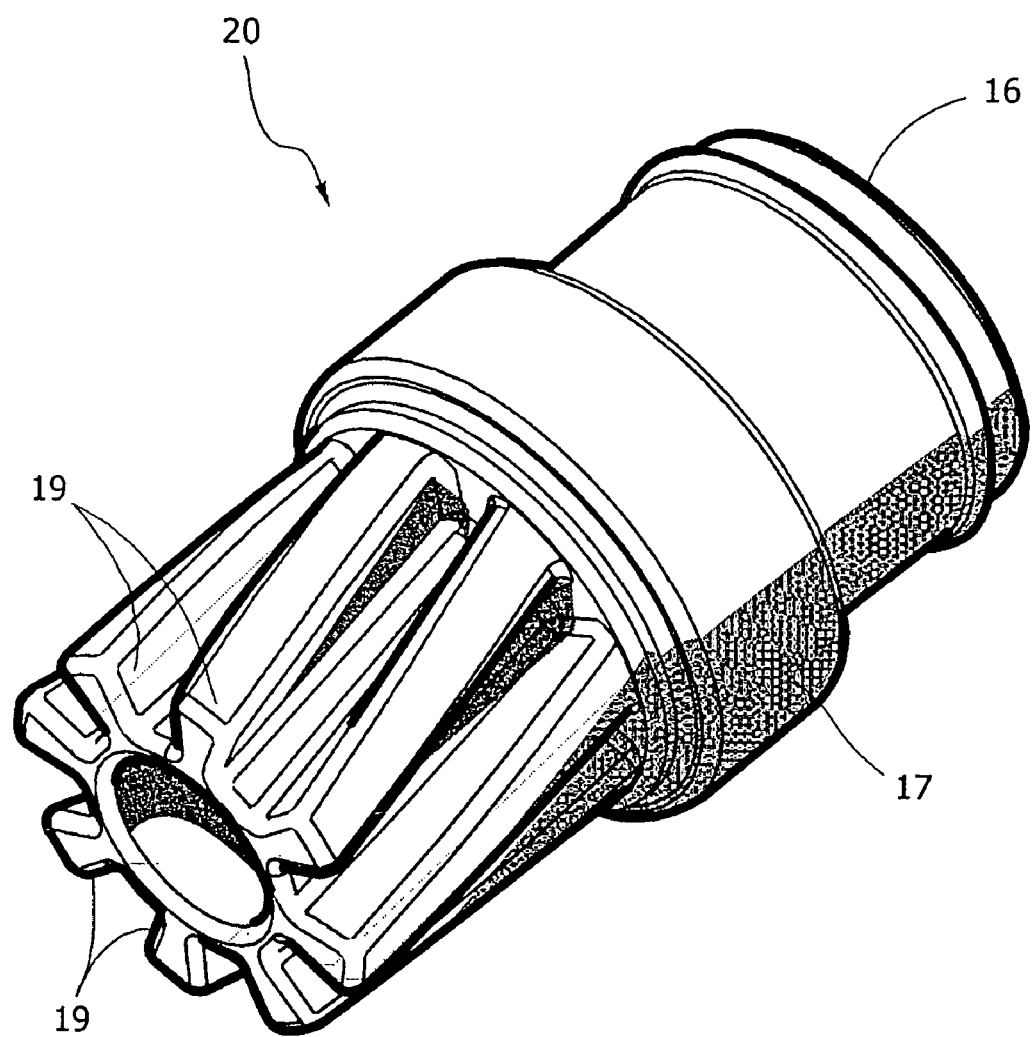
FIG. 6 is a perspective view at a larger scale of the elastic member of the connector.

The elastic sleeve 15 is represented in greater detail in FIG. 6: in the case of the example illustrated it has an end 16 and an annular flange 17 axially facing, respectively, the flange 9 and an axial shank 18 of the fitting 4, and a side wall with helical grooves 19.

Operation of the medical connector set forth above is described in what follows.

When the female luer-lock outlet fitting 4 is in its normal retracted position represented in FIG. 2, the complementary male luer-lock fitting can be easily screwed thereon thanks to blocking in rotation in the direction corresponding to that of screwing of the complementary male luer-lock fitting, performed by the first detent assembly 12-13. Once screwing is completed, unscrewing of the complementary male luer-lock fitting is not allowed as a result of the free rotation in said direction of the fitting 4 with respect to the body 2.

Figure 3:
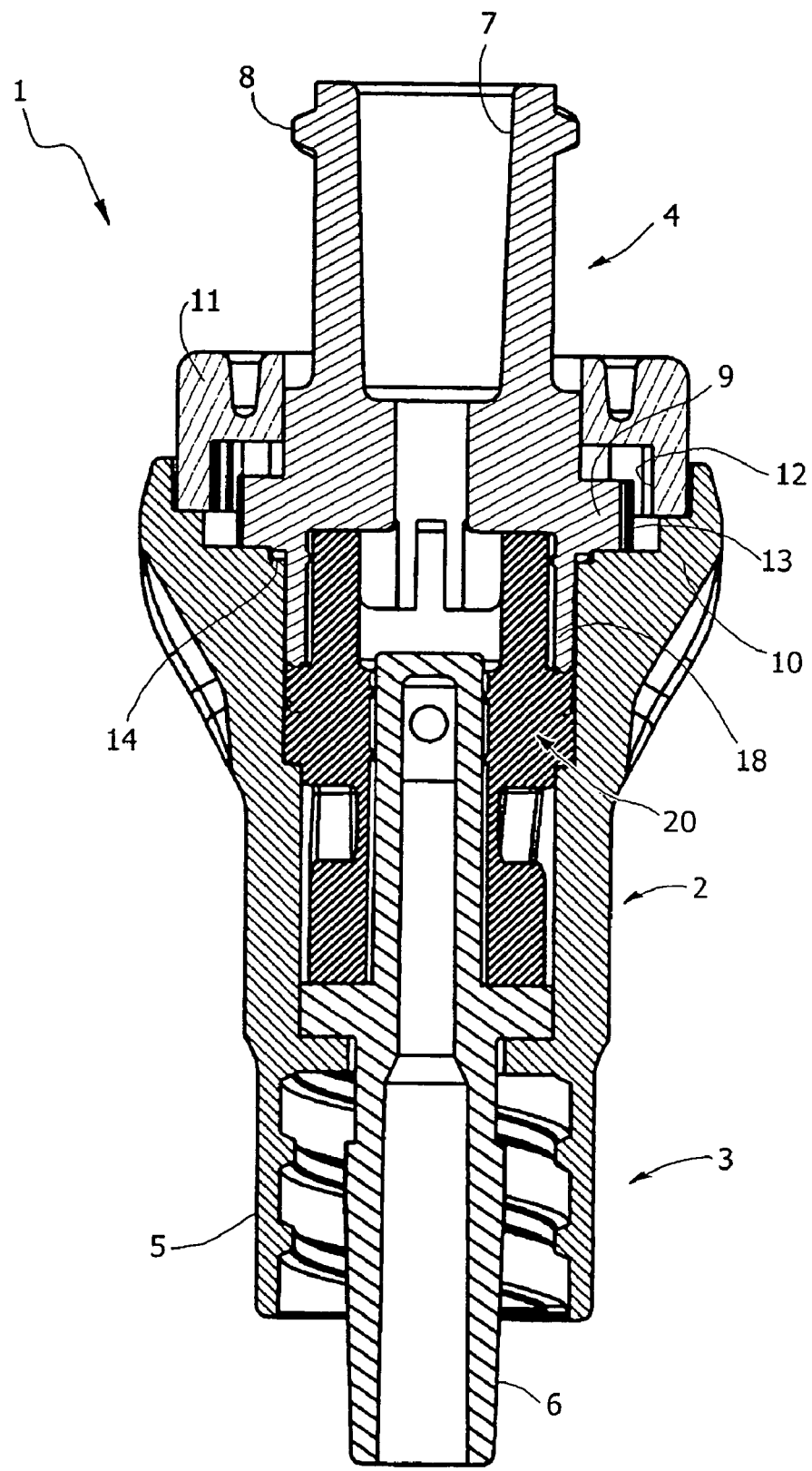
FIG. 3 is a view similar to that of FIG. 1, with the connector in a second operative position.

In order to be able then to unscrew the complementary male luer-lock fitting from the fitting 4 it is necessary to translate the fitting 4 positively in an axial direction from the retracted position of FIG. 2 to the advanced position of FIG. 3. As a result of said translation, engagement of the second detent assembly 14-15 is obtained. In this way, the fitting 4 is blocked in rotation in the direction opposite to the previous one, i.e., in the direction corresponding to that of unscrewing of the male luer-lock fitting, which can in this way be disengaged from the connector 1. It is therefore evident that the detachment between the connector 1 and the medical line cannot occur accidentally, but requires a preliminary voluntary action of axial displacement of the fitting 4 from the retracted position to the advanced one. As soon as said action is removed, the elastic sleeve 20 brings the outlet fitting 4 back into the retracted position of FIG. 2.

It should be noted that, with the arrangement of the inlet fitting 3 described previously, it is possible to provide a further safety function, as a result of which the displacement of the outlet fitting 4 from the retracted position to the advanced one, and hence the consequent possibility of enabling unscrewing of the complementary male luer-lock fitting screwed on the fitting 4 is prevented as long as the inlet fitting 3 is engaged with a corresponding complementary female luer-lock fitting. Said supplementary function, deriving from uncoupling of the internal tubular part 6 of the inlet fitting 3 with respect to the external hollow part 5 and hence from the possibility of axial advance of said tubular body 6 in the direction of the outlet fitting 4, forms the specific subject of the already cited co-pending Italian patent application, filed in the name of the present applicant.

Of course the details of construction and the embodiments may vary widely with respect to what is described and illustrated herein, without thereby departing from the scope of the present invention, as defined by the ensuing claims. Thus, the conformation of the two detent assemblies 12-13 and 14-15 could differ from the one described, providing for example front toothings, conical friction surfaces, or other systems that perform the same function.

What is claimed is:

1. A medical connector comprising:
   a tubular body having an inlet fitting;
   an outlet fitting of the female luer-lock type, said outlet fitting engageable by screwing with a separate complementary male luer-lock fitting in a first rotational direction;
   said female luer-lock outlet fitting being rotatably connected to said body and axially translatable from a retracted position to an advanced position against the action of an elastic thrust element;
   a first detent assembly inhibiting rotation of said outlet fitting relative to said body in said first direction when said outlet fitting is located in said retracted position and said first detent assembly allowing rotation in a second direction opposite to said first direction when said outlet fitting is located in said retracted position;
   a second detent assembly inhibiting rotation of said outlet fitting relative to said body in said second direction when said outlet fitting is located in said advanced position and said second detent assembly allowing rotation in said first direction when said outlet fitting is located in said advanced position.

2. The medical connector according to claim 1, wherein said first detent assembly include a ring of sprung pawls carried by said outlet fitting in a first axial position, and a corresponding ring of saw teeth carried by said body in a first corresponding axial position.

3. The medical connector according to claim 2, wherein said second detent assembly include a ring of saw teeth carried by said outlet fitting in a second axial position staggered with respect to said first axial position, and a corresponding ring of detent teeth carried by said body in a second corresponding axial position.

4. The medical connector according to claim 3, wherein said sprung pawls and said ring of saw teeth are formed integrally with said outlet fitting.

5. The medical connector according to claim 3, wherein said ring of detent teeth is formed integrally with said body, and said ring of saw teeth is formed integrally with a retention collar fixed to said body.

6. The medical connector according to claim 1, wherein said elastic thrust element include a sleeve which is inserted in said body between said inlet and outlet fittings and is axially elastically compressible.

7. The medical connector according to claim 1 wherein said retracted position and said advanced position are spaced axially relative to an axis of said body.

* * * * *